United States Patent [19]

Krönseder

[11] Patent Number: 4,636,635

[45] Date of Patent: Jan. 13, 1987

[54] INSPECTION MACHINE FOR BOTTLES

[76] Inventor: Hermann Krönseder, Postfach 1230, D-8402 Neutraubling, Fed. Rep. of Germany

[21] Appl. No.: 702,242

[22] Filed: Feb. 15, 1985

[30] Foreign Application Priority Data

Feb. 29, 1984 [DE] Fed. Rep. of Germany ....... 3407386

[51] Int. Cl.$^4$ ...................... B07C 5/342; G01N 21/00
[52] U.S. Cl. ................................. 250/223 B; 209/526; 356/240
[58] Field of Search ..................... 250/223 B; 209/524, 209/526, 529, 588; 356/240; 358/106

[56] References Cited

U.S. PATENT DOCUMENTS

| | | | |
|---|---|---|---|
| 3,411,009 | 11/1968 | Ford et al. | 250/223 B |
| 3,651,937 | 3/1972 | Kronseder | 250/223 B |
| 4,241,256 | 12/1980 | Tagaya et al. | 250/223 B |
| 4,280,624 | 7/1981 | Ford | 250/223 B |

Primary Examiner—Edward P. Westin
Attorney, Agent, or Firm—Fuller, House & Hohenfeldt

[57] ABSTRACT

In a bottle inspection machine a cylindrical hollow shaft is driven rotationally about a vertical axis. Another shaft is splined in the tubular shaft for rotation therewith. Another rotor is mounted coaxially to the inner shaft and the two rotors constitute a means for transporting bottles in a circular path. A light source is mounted on the radially outer side of the circular path and projects beams generally radially inwardly through one or more bottles at a time. The bottles carried on the rotors do not fill a complete circle, thus leaving an open side on the rotor. A detector or scanning device is located on the side of the center shaft facing the area which is free of bottles. The scanning device has photodetectors or imaging elements that intercept the images of the bottles side walls which may be modulated by flaws or contaminants in the bottles. The scanning device receives two separate ray bundles or beams from the light source on opposite sides of the center shaft or column which supports the rotor elements. The arrangement provides for good accessibility to the light source and the scanning device.

12 Claims, 6 Drawing Figures

INSPECTION MACHINE FOR BOTTLES

BACKGROUND OF THE INVENTION

This invention relates to a machine through which bottles are passed for inspection and is particularly concerned with improving the devices for inspecting the side walls of bottles for contamination and flaws.

Inspection machines which transport bottles through a circular path while they are being inspected are well known. Typically, the bottles are deposited on a rotary table and their upper portions are engaged by synchronously driven star wheels for stabilizing the bottles as they are carried through a circular path. Generally, there is a source of a beam of light on one side of the bottles and a photodetector array on the other side of the bottles which delivers a control signal that results in ejection of the bottle if the beam is attenuated or dispersed by a contaminant or a flaw. In any case, it is desirable that the bottles do not shift relative to each other as they are transported through the machine and simultaneously rotated. Problems arise, however, as a result of the requirement that the light or radiation source be on one side of the circular path followed by the bottles and the detectors being on the other side because of the large amount of space that is occupied by the rotors and their driving and bearing elements.

In one known type of bottle inspection machine, an upper rotor, constituted by a starwheel, is fixed on a vertical driven shaft and the lower rotor on which the bottles are carried is coupled to the upper rotor with spacer shafts or tie rods. The upper rotor engages the shoulders of the bottles. With this arrangement, space is provided for an illumination source below and radially within the lower rotor which is located on the side of the drive shaft facing away from the bottle-free area of the rotors. A disadvantage of this arrangement is that the area of the bottle shoulder above the lower rotor cannot be scanned and that the positions of the bottles can change because of the lack of guidance at their bases.

In another type of inspection machine, as in the previously mentioned one, the upper rotor is a starwheel fixed on a vertical drive shaft and the lower rotor is a star ring that is connected to the upper rotor by means of spacer shafts. In this particular machine, however, the lower rotor engages the bottles near their bases and the bottles are positioned on continuous belts for rotation as they advance so scanning accuracy is improved. The scanning device used comprises two oscillating mirrors and two photoelectric sensor arrays which are mounted to the side of the driven shaft facing away from the bottlefree area so that there is the disadvantage of poor accessibility. Moreover, the scanning elements are located in an area where they are particularly endangered by bottle fragments. In this connection, it may be noted that the rotors rotated within the upper portion of a large box type machine housing so that even accessibility from below is greatly restricted. In this and other arrangements there is also the disadvantage of not being able to use a lens system that has a long focal length in which case, in accordance with the laws of optics, the depth of field is small.

In another known type of bottle inspection device there is a lower rotor that carries plates or discs on which the bottles are deposited for being transported in a circular path. The supporting discs are oscillated rotationally to assure that the entire bottle wall is disposed within the scanning beam area. In this case, the upper rotor has vertically reciprocable centering bells which engages the bottles at their upper mouth to stabilize them. Both the upper and lower rotors are secured against rotation relative to each other by means of a hollow cylinder provided with scanning slots lying close to the bottles such that the scanning device is located within the hollow cylinder exactly at the rotational axis of the rotors. Accordingly, the scanning device is accessible only after an extensive disassembly of the machine.

Still another known inspection machine for bottles is provided with one spool-shaped rotor that has rollers on its circumference for engaging on the bottle bodies. This rotor operates together with a band traveling in front of an illumination source. The band has rollers which engages the bottle body. Laid transversely through the rotor and its axis of rotation is a bundle of optical fibers rotating with the rotor. The optical fibers conduct light passing through the bottles to several photoelectric sensors fixedly arranged in the bottle-free area of the rotor. Even in this device, the light conductors forming a part of the scanning device within the interior of the rotor are not easily accessible. These light conductors are, furthermore, subject to physical disturbances and require and expensive and complicated structure to overcome the problem. The same is true for the photodetectors which are almost as large as a bottle circumference. Such large elements are expensive and are notable for having low sensitivity. In this machine, where bottles are pushed along through rollers over a stationary sliding surface, precise and disturbance-free transportation is impossible.

One object of the present invention is to substantially improve the accessibility of the scanning apparatus without loss of inspection accuracy. According to the invention, upper and lower rotors are connected only by coaxial shaft means constituting a column which may have a relatively small diameter. The column is central and coaxial with the rotors and is in an area free of rotating bottles. The bottles are transported in a series along a circular path defined by the rotor. A source of an illumination beam for the bottles is located radially outwardly from the circular path of the bottles and directs two light beams through the bottles in a direction generally toward the central support column for the rotors. In one embodiment, the detectors which receive the light beams that define an image of the bottle wall are diametrically opposite from the source of the light beams. The light beams pass the columns on diametrically opposite sides. In this embodiment, only about 180° of the rotor is occupied by bottles so as to leave an open space on the side of the rotor at which the photodetectors or image detecting means are located. Thus, the two beams from the light source pass on opposite side of the central column, through the open space and outwardly from the rotor to a pair of oscillating mirrors which intersect light beams that, in this embodiment, have passed through two different bottles and these mirrors reflect the light beams which are modulated by the bottle walls and flaws and contaminants thereon, toward the detectors.

Another embodiment, especially applicable to machines having rotors of lesser diameter than the one mentioned in the preceding paragraph, also has the source of two light beams that pass through respective bottles on the radially outward side of the rotor. In this case, where the transported bottles occupy a major part of the circular path through which they are conveyed, the two light beams project past opposite sides of the central column. In this case, there are two oscillating mirrors and a pair of photodetector or image receiving means that are mounted on the opposite side of the central column from the light source but within the circular path through which the bottles are conveyed.

In still another embodiment, where the rotor diameters are smaller than in either of the two preceding cases, the light source is again located radially outwardly from the circular path through which the bottles are conveyed. Only one bottle at a time is aligned with the beams but the beams are projected in two paths that diverge from each other thereby pass opposite sides of the central column. Mirrors are arranged on opposite sides of the central column to reflect the beams to respective detectors which will produce a reject signal if either of the beams is modulated by a flaw or contaminant. In this embodiment, as opposed to the two preceding embodiments, the bottles are not rotated about their vertical axes as they sweep through the light beam. Instead, the bottles are carried on a rotor which has shallow pockets for retaining them.

The various structural features which contribute toward increasing inspection accuracy and accessibility of the scanning system components will now be described in detail in reference to the drawings.

DESCRIPTION OF THE PREFERRED EMBODIMENT

The bottle inspection machines depicted herein are adapted for inspection of bottles that are transparent and symmetrical about their vertical axes.

Figure 1:
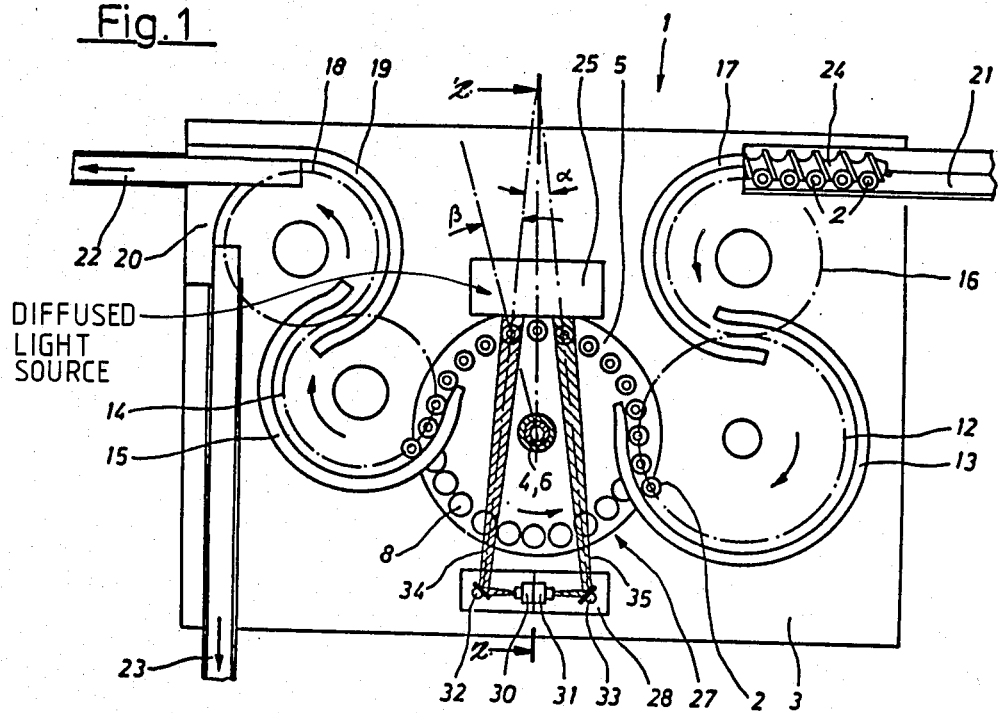
FIG. 1 is a plan view of a bottle inspection machine as seen from below the upper rotor which is not shown in this view.

In FIG. 1, the bottle inspection machine is generally designated by the numeral 1. The bottles are marked 2. The machine comprises a box-shaped housing or base 3 in which a vertical rotatable driven hollow shaft 4 is located. A lower bottle transporting rotor 5 is fastened to hollow shaft 4 for rotation therewith. Lower rotor 5 resembles a spoked wheel. Within hollow shaft 4 there is a further shaft or column 6 which is vertically adjustable. The two shafts may be splined so they rotate together. A drum-shaped upper rotor 7 is fixed on the upper end of shaft of column 6. The drive means for the coaxial shafts 4 and 6 which turn the rotors are not shown but it will be understood that upper rotor 7 is driven synchronously with lower rotor 5.

Lower rotor 5 rotates over a stationarily supported cam plate 10 in which there is a closed-loop cam groove at varying radial distances from the center of rotation of shaft 4. The cam groove causes some cranks 9 to oscillate and rotate the bottles as they are being transported in a circular path through the inspection zone of the machine. The lower rotor 5, thus, has circumferentially spaced apart plates or dishes 8 on which the bottom of the bottles 2 rest as they are being oscillated about their vertical axes and transported in a circular path through the machine. With this construction a precise positioning and automatic rotation of the bottles is achieved as the rotors 5 and 7 rotate. In the upper rotor 7 there are a plurality of controlled liftable and lowerable centering bells 11 which are timed to come down and engage the mouth of each bottle as it is deposited on lower rotor 5.

Bottles that are to be inspected are fed into the machine on a closed loop conveyor belt 21 which moves in the direction of the arrow and terminates tangentially to an infeed starwheel 16. The series of bottles 2 are engaged by a feed screw 24 which establishes a fixed distance between consecutive bottles so they are deposited in good order onto starwheel 16. The starwheel has a circular guide plate 17 about part of its periphery for retaining the bottles as they are moved through an arc of about 180° in the direction indicated by the arrow on the starwheel 16. Starwheel 16 is driven synchronously with another starwheel 12 that is provided with a curved guide 13 for retaining the bottles in the pockets of the starwheel. Rotation of starwheel 12 advances the bottles to the lower rotor 5 which is also rotating in the direction of the arrow on it at a fixed speed relative to the rotational speed of intermediate starwheel 12. The place where starwheel 12 and rotor 5 overlap in FIG. 1 is the bottle infeed station for the rotor. Intermediate starwheel 12 is so synchronized with rotor 5 that one bottle after another will be transferred to the bottle supporting plates 8 on the rotor exactly at the right time for the bottle to be centered on the plate. As can be seen in FIG. 1, the bottles are carried around on the oscillating bottle supporting plates on lower rotor 5 in a circular path that subtends an arc of somewhat more than 180°. After the bottles on the rotor 5 have undergone inspection, they are discharged at a discharge station to an intermediate starwheel 14, rotating in the direction of the arrow thereon, which is next to a curved bottle retaining guide 15. The inspected bottles are transferred from starwheel 14 to a discharge starwheel 18 which has a bottle retaining guidewall 19. There are two conveyor belts 22 and 23 associated with discharge starwheel 18. One of them receives bottles that have passed inspection and the other receives those which have not and are to be rejected. The means for directing satisfactory bottles onto one conveyor 22 or 23 and reject bottles onto the other is well known and need not be described. It is sufficient to say that when the inspections devices, yet to be described, detect a defective bottle, a reject signal is generated such that when the bottle becomes aligned on the discharge starwheel 18 with the conveyor 22 or 23 for rejects, an ejector mechanism, not shown, is actuated to push the defective bottle onto the reject conveyor while letting the good ones pass.

It should be noted that adjacent the infeed starwheel 16 there is a synchronously driven feed screw 24 which separates the bottles transported on conveyor belt 21 by the proper distance for them to register properly in the pockets of infeed starwheel 16.

Through the previously mentioned conveying members 5, 7, 12-20 and 24, the bottles 2 are positioned exactly evenly at high speeds of, for example, 60,000 bottles per hour and moved through the inspection machine and its various inspection zones free from any unwanted disturbances.

Figure 2:
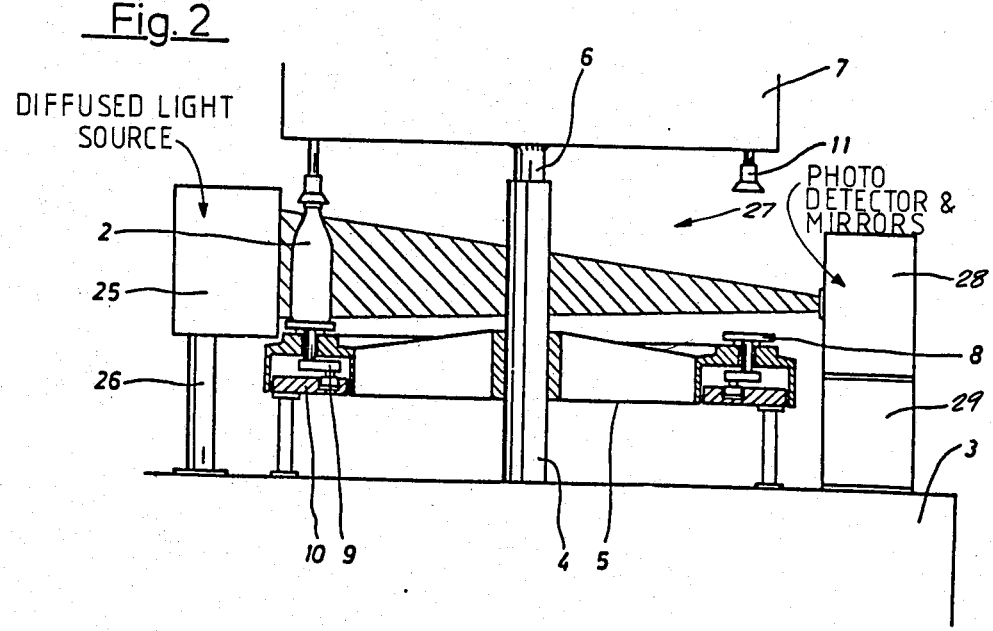
FIG. 2 is a vertical section taken on a line corresponding with 2—2 in FIG. 1.

In the FIGS. 1 and 2 embodiment, in the area of the lower 5 and upper 7 rotors where the bottles are clamped tightly between the rotary plates 8 and the centering bells 11, the bottles are moved on a circular path of somewhat more than 180° so the entire side wall of each bottle is completely accessible. As can be seen in FIG. 1, on the radially outer side of that part of the circular path which is occupied by bottles, there is a source 25 of radiation such as light which is supported on a column 26 that stands on the top of machine base 3. Source 25 has, for example, two projector lamps, not shown, which project light beams through slots whose vertical heights are substantially equal to the height of each bottle and which simultaneously illuminate and penetrate the side walls of two bottles. It should be noted that the light beam source 25 is easily accessible on the inspection machine 1 in the very open region between inlet starwheel 16 and discharge starwheel 18.

In FIG. 1 the two light beams projected from source 25 are marked 34 and 35. Since bottles are present in a circular path or arc that subtends a little more than 180°, a large angular region 27 between the upper rotor 7 and lower rotor 5 is free of bottles to allow the beams 34 and 35 to pass beyond the periphery of the rotors substantially diametrically opposite of the light source 25. Beams 34 and 35 which may or may not be modulated by contaminants or flaws in the bottles are directed along opposite sides of central column 4, 6 and impinge upon oscillating mirrors 32 and 33 such that beam 34 is reflected into a photodetector 30 and beam 35 is reflected into a photodetector 31. The oscillating mirrors 32 and 33 and the photodetectors 30 and 31 constitute a scanning device that is designated generally by the reference numeral 28. The mirrors and detectors are on opposite sides of a vertical mid-plane running through central column 4, 6 and the mid-point of light source 25. The scanning device, as can be seen in FIG. 2, is mounted to a bracket 29 which is fixed on the top machine base 3. The photodetectors 30 and 31 have images of the bottle side walls focused on their detector elements. The detectors or image converters 30 and 31, in a commercial embodiment, comprise a closely packed vertical column of photosensitive elements such as photodiodes arranged behind a lens. The oscillating mirrors 32 and 33 deflect the light beams 34 and 35 through an acute angle of about 85 degrees. The mirrors 21 and 22 are oscillated synchronously with the rotational movement of rotors 5 and 7 in such manner that they rotate for a short time with the bottles 2 in front of the light source 25. The deflected optical axes of the two photodetector devices 30 and 31 extend back toward the light sources on opposite sides of the center column 4, 6 and intersect at a central acute angle, alpha, of about 10° to the common radially center plane of the illumination device 25 and scanning device 28. Thus, the beams intersect the circular path of the bottles 2 at a central acute angle, beta, of about 20°. The center column 4, 6 lies in the middle between the two beams or bundles of rays 34 and 35 which emanate from the two bottles being tested and are received by the photodetector devices 30 such that the beams never undergo any interference. The scanning device 28 is easily accessible on the rear side of the inspection machine 1.

The cam plate 10 for oscillating and controlling the rotational angles of the bottle supporting plates 8 is constructed in such manner that the bottles 2 during their first scanning by means of photodetectors 30 and their second scanning by means of detectors 31 are continuously rotated in each case through 180° so that the entire bottle circumference of 360° is scanned. In the area between the two scanning positions in FIG. 1, each bottle 2 stands still for a short time or a slight corrective rotation takes place.

Figure 3:
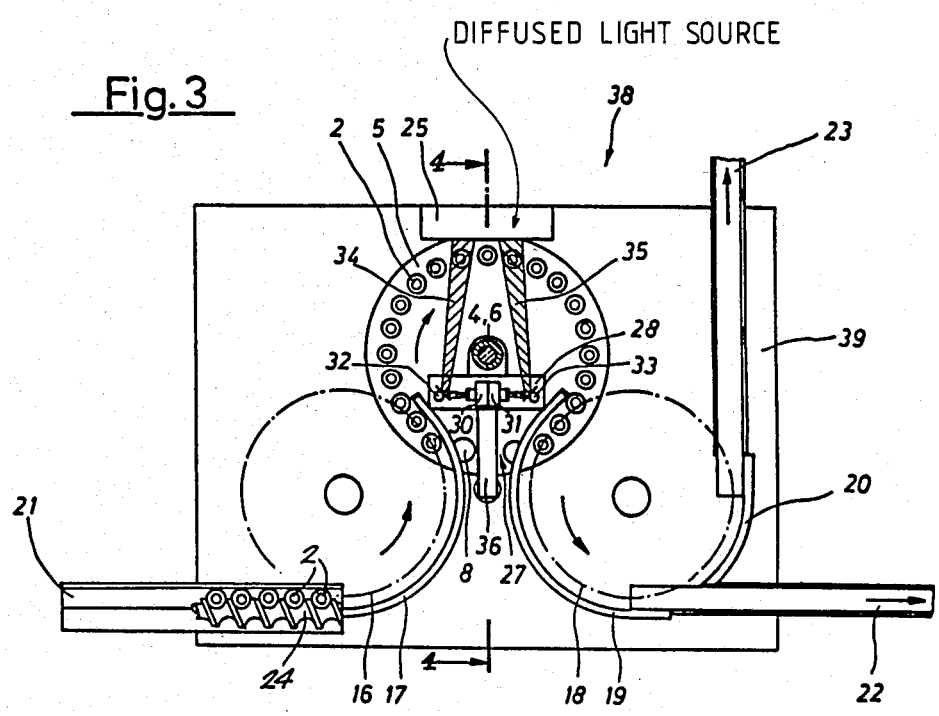
FIG. 3 is a plan view of another embodiment of a bottle inspection machine as viewed from below the upper rotor which is omitted.
Figure 4:
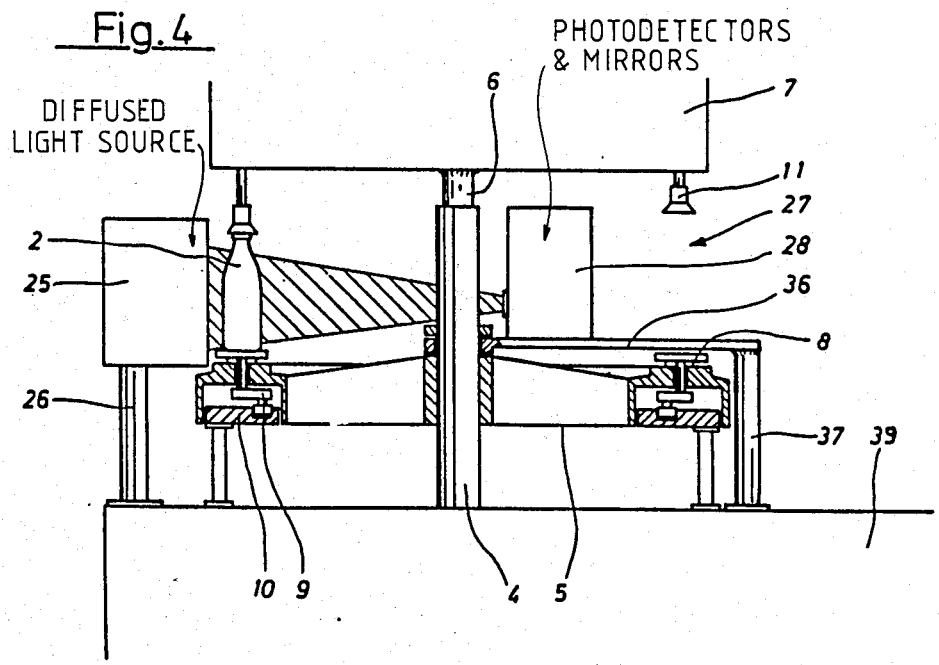
FIG. 4 is a vertical section taken on a line corresponding with 4—4 in FIG. 3 and also showing the upper rotor.

Shown in FIGS. 3 and 4 is a bottle inspection machine which is smaller than the one just described in connection with the preceding two FIGURES and is designated generally by the reference numeral 38. Parts in the FIGS. 3 and 4 machine which are similar to those in the FIGS. 1 and 2 machine are given the same reference numerals. The base or housing 39 of the inspection machine in FIGS. 3 and 4 is somewhat smaller than the housing 3 in the preceding FIGURES. In FIG. 3 and 4, there is an infeed conveyor 21 at whose end there is a worm or feed screw 24 which advances the incoming bottles to an infeed starwheel 16. The bottles are retained in the pockets of starwheel 16 by curved guide wall 17. The bottles are transferred directly from infeed starwheel 16 to rotor 5 which can be identical in structure and function, but possibly not in diameter to rotor 5 in the FIG. 1 and 2 embodiments. As can be seen in FIGS. 3 and 4, the light source or illumination device 25 is again located at the rear side of the inspection machine 38 and is readily accessible. In this embodiment, the circular path on the rotor which is occupied by bottles, subtends an angle of about 270°, leaving an arc or zone 27 of about 90° between the bottle infeed and discharge stations of the rotor free of bottles. The scanning device having the photodetector means 30, 31 and the oscillating mirrors 32, 33 is again on a side opposite of center column 4, 6 from the light source 25. The oscillating mirrors 32 and 33 are on opposite sides of the mid-plane running through central column 4, 6 and the mid-point of light source 25. Hence, the beams 34 and 35 that have traversed two different bottles simultaneously again pass center column 4, 6 on opposite sides without the column shadowing any part of the bottle side wall image beams. In the FIG. 3 and and 4 embodiment, the detector or scanning device 28 is again on the same side of the central column as is the bottle-free zone on the rotors although in the FIG. 3 embodiment the device 28 is radially within the path of rotation of rotors 5, 7.

The scanning device 28 is fixed on a plate 36 which is supported and journalled on hollow shaft 4 of the center column and is suspended out by means of an arm into the bottle-free area 27 between rotors 5 and 7. This arm is connected to a supporting column 37 which is fixed to the horizontal top of housing 39. The mounting comprised of column 37 and plate 36 for the scanning device 28 results in the scanning device being held stable in the bottle-free area 27 between the rotors 5 and 7. It is to be noted, however, that the scanning device 28 is easily accessible through the bottle-free area 27.

Figure 5:
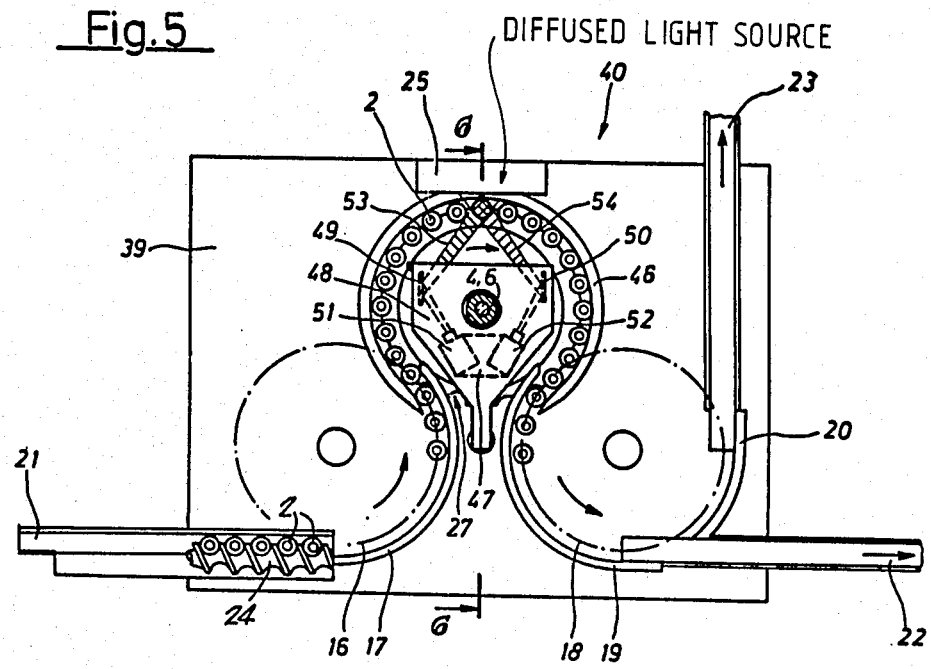
FIG. 5 is a plan view of another embodiment of a bottle inspection machine as viewed from below the upper rotor which is omitted.
Figure 6:
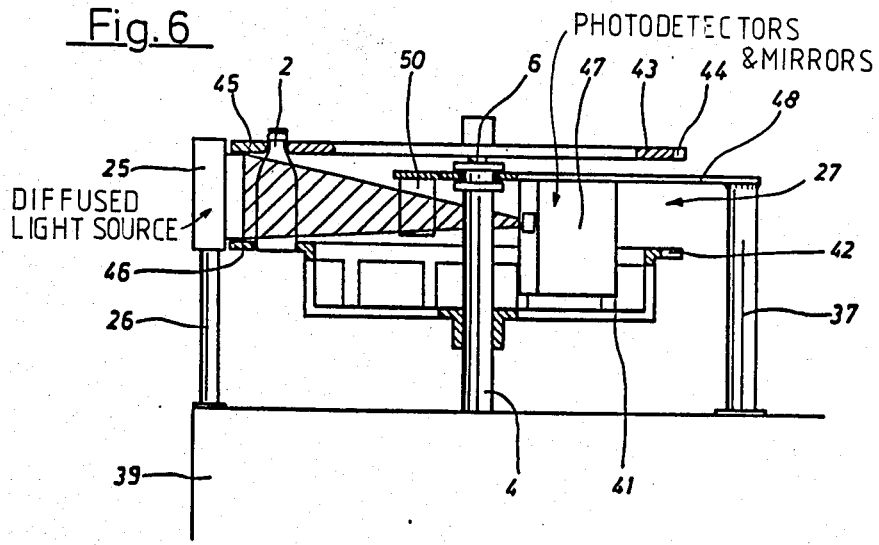
FIG. 6 is a vertical section taken on a line corresponding with 6—6 in FIG. 5 and showing the upper rotor.

The inspection machine 40 in FIGS. 5 and 6 corresponds in some respects with the machine 38 in FIGS. 3 and 4. Only the differences between the embodiments will be described. In machine 40, there is a center column comprised of a hollow rotational driven shaft. A lower rotor 41 is fixed to shaft 4. Rotor 41 is bucket-shaped and is provided on its periphery with pockets 42 for bottles 2. On the inner shaft 6 of the center column a disc-shaped rotor 43 is fixed. Inner shaft 6 can be splined in shaft 4 so both shafts are driven rotational together but vertical adjustment of shaft 6 is provided for to accommodate bottles of different heights. Upper rotor 43 also has pockets for receiving the necks of bottles 2. The two rotors 41 and 43 comprise a starwheel by which the bottles 2 are moved in a circular path of about 270° in the machine. The bottles are fed from infeed conveyor belt 21 to an infeed starwheel 16 wherein the bottles are guided by a guide wall 17. The bottles are transferred at the rotor infeed station directly from infeed starwheel 16 to successive circumferentially spaced apart pockets 42 in the bucket-shaped lower rotor 41. The bottles, after having passed through a circular path of over 270° as they are conveyed on the starwheel composed of rotors 41 and 43, are transferred at a rotor discharge station to a discharge starwheel 18 where they pass an ejector mechanism, not shown, which is activated automatically to eject defective bottles onto one of the conveyors 22 or 23 while allowing the good bottles to pass to the other of the conveyors. The lower rotor 41 is formed as a spoked wheel so that fragments of any broken bottles can fall down onto the top of the base or housing 39 for the machine.

The light source 25 is again located on the outer side of the circular path through which the bottles undergoing inspection are transported. A circular guide member 46 surrounds the bottles as they are transported by the rotors comprising the starwheel. The scanning device 47 is located again on the side of center column 4, 6 adjacent the bottle-free area 27 and within the path of rotation of rotors 41 and 43. The scanning device 47 is fixed on the lower side of a plate 48 which is supported at one end by journalling it on rotatable hollow shaft 4 and on the other end is supported on a column 37 which is mounted to the top of machine base 39. As can be seen in FIGS. 5 and 6, the scanning device 47 is easily accessible through the bottle-free side of the rotor. The two photodetectors devices 51 and 52 of scanning device 47 are comprised of a photodiode array or column, not shown, on which the bottle images are focused so that they may receive complete images of a bottle side wall. The detectors are arranged with the optical axes inclined to one another at an acute angle in such manner that the center column 4, 6 lies between the optical axes. In front of each photodetector array, a stationary mirror 49 and 50 is fixed on plate 48. The mirrors deflect the optical axes at an obtuse angle so that the axes of the two image converters or photodetector arrays 51 and 52 intersect at the center axis of the bottle to be scanned and within the radial center plane of the light source 25 and the scanning device 47. In the FIG. 5 and 6 embodiment, no automatic rotation of the bottles 2 is necessary nor is it necessary to oscillate the mirrors 49 and 50 since the two image converters or photodetector arrays 51 and 52 cover the entire bottle wall simultaneously. It is also possible to arrange the mirrors so that only one image converter such as 51 or 52 can be used. In such case, the photodiode array on which the two bundles of rays or beams 53 and 54 impinge both come from the bottle at different angles but the images are superimposed. Nevertheless, the beams would be modulated by any flaws or contaminants that are present in the bottles.

As indicated earlier, only the scheme for inspecting the side walls of bottles in an inspection machine are new and are described herein. It will be understood, however, that in addition to the scanning devices 28 and 47 for the side walls of bottles other scanning and control devices, not shown, are usually present for inspecting the bottoms of the bottles for contaminants and flaws and for undesirable liquid residuals in the bottles, for example. Thus, a single inspection machine is used for detecting all aspects of bottle integrity and cleanliness before the bottles are passed on to a filling machine.

I claim:

1. A machine for inspecting bottles for contaminants, flaws and the like, comprising:

shaft means arranged concentrically for being driven rotationally concurrently about a vertical axis, upper and lower rotor means fastened to said shaft means, respectively, in vertically spaced apart relationship for being driven at the same rotational speed, said upper rotor means having means arranged in a circle for engaging the upper ends of bottles and said lower rotor means having correspondingly arranged means for engaging the bases of said bottles, respectively, said rotor means transporting said bottles in a circular path between a bottle infeed station and a bottle discharge station, said stations being located such that there will be a part of said path free of bottles between said discharge and infeed stations, radiation source means located radially outwardly of the circular path in which the bottles travel on said rotor means between said infeed and discharge stations, said source means being constructed and arranged to project two beams of radiation having substantially the height of a bottle across said path through at least one bottle, said beams diverging from each other so as to pass said shaft means on opposite sides of said shaft means toward the part of said circular path that is across the rotor means from said source means and is free of bottles, and photoresponsive scanning means arranged in alignment with said part of the circular path that is free of bottles to receive said beams, said scanning means responding to said beams being modulated by flaws, contaminants and the like in said bottle by producing a signal indicative thereof.

2. The machine according to claim 1 wherein said scanning means is located radially outwardly from said rotor means and from said part of said circular path that is free of bottles.

3. The machine according to claim 1 wherein said scanning means is radially within the peripheries of said rotors and radially within said part of said circular path that is free of bottles.

4. The machine according to any one of claims 1, 2 or 3 wherein said shaft means comprises one hollow rotationally driven shaft to which said lower rotor means is fastened and an inner shaft within and extending from said hollow shaft to which inner shaft said upper rotor means is fastened, said inner shaft rotating jointly with the hollow shaft and being adjustable axially in said hollow shaft to thereby change the spacing between said rotor means as required to accommodate bottles of different heights.

5. The machine according to claim 1 including: a machine base upwardly from which said shaft means which turns said rotor means extends, mounting means for said scanning means comprising a plate member extending between said upper and lower rotor means with the plane of said member perpendicular to the axis of rotor means rotation, said scanning means being mounted to said plate member, and members fastened to said plate member and machine base for supporting said plate means.

6. The machine according to claim 1 wherein said scanning means comprises:
two mirrors each of which is located in the path of a beam on opposite sides of a vertical plane extending through the axis of said shaft means and substantially the midpoint of said part of said circular path that is free of bottles, and
two photodetector means respectively on opposite sides of said plane and on the side of said shaft means that is presented toward the bottle-free part of said circular path.

7. A machine for inspecting bottles for contaminants, flaws and the like, comprising:
shaft means arranged for being driven rotationally about a vertical axis,
upper and lower rotor means fastened to said shaft means in vertically spaced apart relationship for being driven at the same rotational speed, said upper rotor means having means arranged in a circle for engaging the upper ends of bottles and said lower rotor means having correspondingly arranged means for engaging the bases of said bottles, respectively, said rotor means transporting said bottles in a circular path between a bottle infeed station and a bottle discharge station, said stations being located such that there will be a part of said path free of bottles between said discharge and infeed stations,
radiation source means located radially outwardly of the circular path in which the bottles travel on said rotor means between said infeed and discharge stations, said source means being constructed and arranged to project two beams of radiation simultaneously through at least one bottle and respectively on opposite sides of shaft means toward the part of said circular path that is across the rotor means from said source means and is free of bottles, and
scanning means responding to said beams being modulated by flaws, contaminants and the like in said bottle by producing a signal indicative thereof, said scanning means including two mirrors each of which is located in the path of a beam on opposite sides of a vertical plane extending through the axis of said shaft means and substantially the midpoint of said part of circular path that is free of bottles,
said mirrors being mounted for being driven oscillatingly about a vertical axis to synchronously follow the bottles as they pass through said radiation beams from said source,
and two photodetector means on opposite sides of said vertical plane on the side of said shaft means that is presented toward the bottle free part of said circular path, said photodetector means producing said signal.

8. The machine according to claim 1 wherein said scanning means comprises:
two mirrors each of which is located in the path of a beam on opposite sides of a vertical plane extending through the axis of said shaft means and the midpoint substantially of the part of said circular path that is free of bottles, and
a single photodetector means located substantially in said plane and on a side of said shaft that is presented toward said bottle-free part of said circular path for said photodetector means to receive both beams simultaneously after the beams are reflected by said mirrors, respectively.

9. The machine according to claim 1 wherein said means on said lower rotor means for engaging the bases of the bottles are comprised of plates on which said bottles are supported as they are transported in said circular path, and
means for rotating said plates and any bottle thereon as said bottle passes through a radiation beam from said source.

10. The machine according to claim 9 wherein said means on said upper rotor means for engaging the upper ends of said bottles comprise a plurality of centering bells each of which is driven downwardly to engage the end of a bottle at said infeed station and driven upwardly to release said bottle at said discharge station.

11. The machine according to any one of claim 1, 2 or 3 wherein said upper rotor means comprises a disk having circumferentially spaced apart pockets in its periphery for said engaging of the upper ends of said bottles.

12. The machine according to any one of claims 1, 2 or 3 wherein said lower rotor means is constructed as an open-topped bucket having a radially extending flange in which there are pockets for said engaging of said bases of the bottles, and
said photoresponsive scanning means are suspended in said bucket.

* * * * *